United States Patent
Pietrini et al.

(10) Patent No.: US 6,749,631 B1
(45) Date of Patent: Jun. 15, 2004

(54) CAPSULAR BAG RING AND AN ASSEMBLY CONSTITUTED BY SUCH A RING AND AN INJECTOR THEREFOR

(75) Inventors: Pascal Pietrini, Nantes (FR); Lionel Jeannin, Choisy (FR)

(73) Assignee: Corneal Industrie, Pringy (FR)

( * ) Notice: Subject to any disclaimer, the term of this patent is extended or adjusted under 35 U.S.C. 154(b) by 0 days.

(21) Appl. No.: 10/130,570

(22) PCT Filed: Nov. 17, 2000

(86) PCT No.: PCT/FR00/03195

§ 371 (c)(1),
(2), (4) Date: May 17, 2002

(87) PCT Pub. No.: WO01/35868

PCT Pub. Date: May 25, 2001

(30) Foreign Application Priority Data

Nov. 19, 1999 (FR) ............................................. 99 14570

(51) Int. Cl.[7] .................................................. A61F 2/16
(52) U.S. Cl. ...................... 623/6.12; 623/6.39; 623/6.4; 606/107
(58) Field of Search ................................ 623/4.1, 6.12, 623/6.39, 6.4, 6.41, 6.42, 905, 907; 606/107

(56) References Cited

U.S. PATENT DOCUMENTS

| 5,098,443 | A | * | 3/1992 | Parel et al. ................. | 128/898 |
| 5,242,449 | A | * | 9/1993 | Zaleski ........................ | 606/107 |
| 6,319,282 | B1 | * | 11/2001 | Nishi ........................ | 623/6.39 |
| 6,413,277 | B1 | * | 7/2002 | Neuhann ..................... | 623/6.39 |

FOREIGN PATENT DOCUMENTS

| DE | 0884031 A1 | * | 5/1998 | ............. A61F/2/16 |
| EP | 0544948 | | 6/1993 | |
| EP | 0884031 | | 12/1998 | |
| FR | 2754173 | | 4/1998 | |

* cited by examiner

Primary Examiner—David J. Isabella
Assistant Examiner—Kamrin Landrem
(74) Attorney, Agent, or Firm—James Ray & Associates

(57) ABSTRACT

The invention relates to a ring (10) for a capsular bag, the ring being constituted by a curved elongate element presenting substantially constant thickness and having inner and outer edges. The elongate element comprises a first branch (30) extending between a first end (20) and a point B, and a second branch (32) extending between said point B and a second end (22), said outer edge of the elongate element when at rest and in its plane of symmetry being disposed substantially at a point A tangentially to a circle of center O and of radius R not less than the radius of the capsular bag, the outer edge of said first branch being defined by a portion of a circle of center O' and of radius R', where R<R'<1.10R, the outer edge of the second branch of said elongate element being defined by a portion of a hyperbolic spiral of center O and connected tangentially to said portion of a circle at said point B.

10 Claims, 4 Drawing Sheets

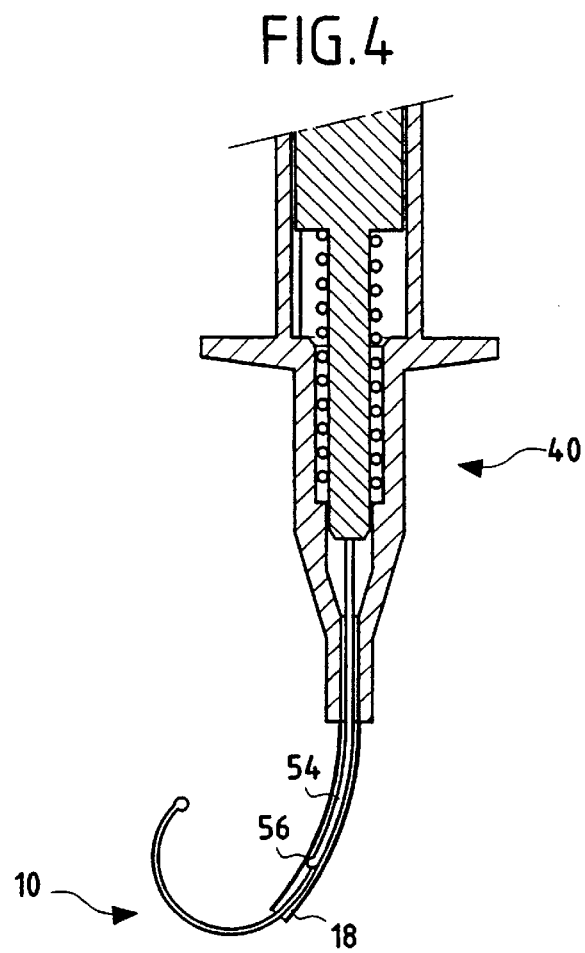
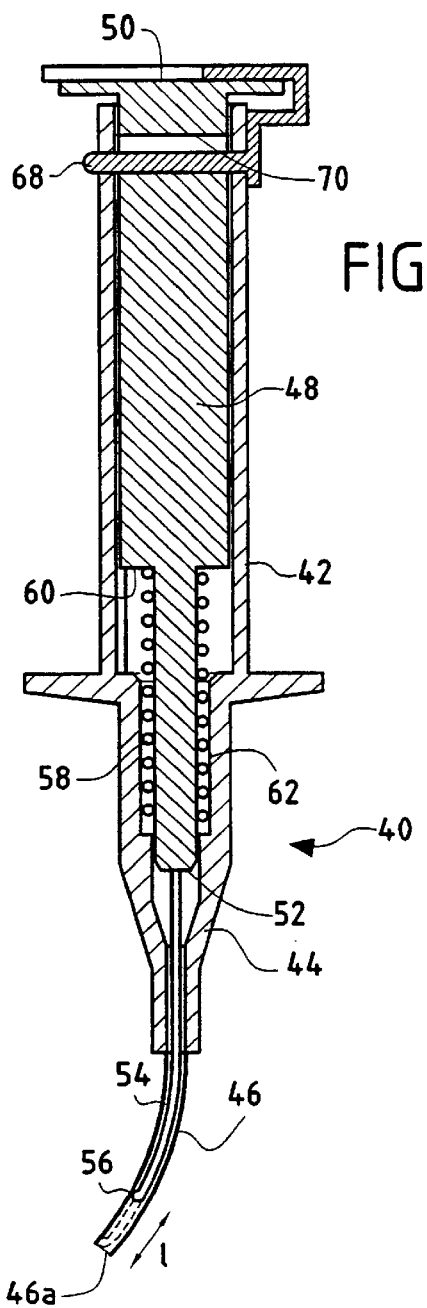
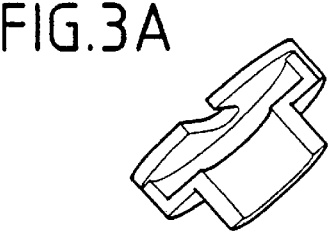
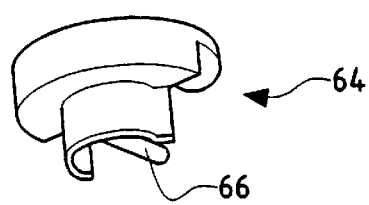

CAPSULAR BAG RING AND AN ASSEMBLY CONSTITUTED BY SUCH A RING AND AN INJECTOR THEREFOR

FIELD OF THE INVENTION

The present invention relates to a capsular bag ring and to an assembly constituted by such a ring and an injector therefore.

More precisely, the invention relates to an elastically deformable ring for putting into place in the capsular bag after removal of the natural lens in order to maintain the natural circular shape of the capsular bag, and particularly but not exclusively in order to make it easy subsequently to put an intraocular implant into place in the capsular bag.

BACKGROUND OF THE INVENTION

It is known that the so-called "cataract" operation consists in removing the lens while conserving the covering of the lens which is referred to as the capsule or capsular bag. However since the bag is made of a very fine membrane which is connected to the inside wall of the eye via a ring of fibers known as zonules, the membrane tends not to conserve its regular uniform circular shape.

It is also known that after the lens has been removed, an intraocular implant is put into place in the capsular bag, which implant consists essentially in an optical portion of substantially circular shape and an elastically deformable haptic portion which serves to center the optical portion of the intraocular implant in such a manner that its optical axis coincides substantially with the optical axis of the eye. To ensure that the haptic portions perform their functions adequately, i.e. that they hold the optical portion of the implant in a central position, it is necessary for the periphery of the capsular bag, against which the free ends of the haptic portions press, to retain its circular shape and in particular it is important to avoid folds forming in the capsular bag, so as to avoid complications such as zonules being torn or the capsular bag shrinking.

To keep the capsular bag in a circular shape, proposals have already been made to install a resilient ring, usually made of polymethylmethacrylate (PMMA) whose elastic expansion serves to keep the capsular bag circular in shape. As a subsidiary point, the pressure exerted by the ring on the membrane constituting the capsular bag serves to avoid or at least limit the proliferation of parasitic cells that can obscure the capsular bag and thus degrade the patient's vision. Such capsular bag rings are described in particular in European patent application No. 0 884 031. The ring described therein is symmetrical in shape. That shape does not make it possible to prevent folds forming in the capsular bag while the ring is being put into place. In addition, that shape does not make it possible to obtain substantially identical pressure over the entire periphery of the capsular bag.

BACKGROUND OF THE INVENTION

An object of the present invention is to provide a capsular bag ring of a shape that facilitates insertion into the capsular bag without causing folds to form therein, and that enables the pressure exerted by the ring on the periphery of the capsular bag to be distributed better and thus more effectively so as to further improve maintenance of the natural circular shape of said capsular bag.

To achieve this object, the invention provides a capsular bag ring constituted by a curved elongate element presenting a first end and a second end provided with handling means, said elongate element presenting a plane of symmetry, thickness that is substantially constant in a direction orthogonal to said plane of symmetry, and inner and outer edges, said outer edge of the elongate element when at rest and in its plane of symmetry being disposed substantially tangentially at a point A to a circle of center O and of radius R that is not less than the radius of the capsular bag, said outer edge being located at the outside of said circle, said ring being characterized in that said elongate element further comprises a first branch extending between said first end and a point B, and a second branch extending between said point B and said second end, said elongate element being of a length that is substantially not less than the length of the perimeter of said circle of center O, the outer edge of said first branch being defined by a portion of a circle of center O' and of radius R', where R<R'<1.10R, and in that the outer edge of the second branch of said elongate element is defined by a portion of a hyperbolic spiral of center O and joining tangentially with said portion of a circle at said point B, close to said tangential point A, whereby:

the length of any segment joining the center O to a point M' of the outer edge of the second branch is greater than the length of the segment joining the center O of the circle to a point M of the outer edge of the first branch, the point M being such that the angle between the segment OM and the median diameter joining the center O to the tangential point A is equal to the angle between the segment OM' and said median diameter; and the radius of curvature at any point M' of the outer edge of the second branch is greater than the radius R'.

It will be understood that the ring comprises a first branch substantially in the shape of a circular arc whose radius is slightly greater than that of the capsular bag and a second branch in the form of a portion of a hyperbolic spiral. The first branch is the branch that is inserted first into the capsular bag. Because this branch corresponds more or less to a semicircle of radius close to that of the capsular bag, it is easy to put this first branch into place in the capsular bag. It is only when the second branch of spiral shape is introduced into the capsular bag that the ring is subjected to significant elastic deformation of its second branch. In addition, because of its hyperbolic spiral shape, the extra diameter of the ring in said second branch compared with the diameter of the capsular bag increases only progressively. This makes it easier to put the second branch of the ring into place and thus to put the entire ring into place, since the second branch is compressed progressively.

In addition, since the elastic deformation of the ring which serves to keep the capsular bag in shape is distributed along the second branch of the ring which corresponds substantially to a semicircle, distribution of the stresses applied to the capsular bag is encouraged, thereby avoiding the risk of folds forming in said bag.

Another problem which arises is that of how to insert the ring inside the eye and the capsular bag. To do this, it is known to use an injector which is terminated by a cannula of small diameter so as to enable it to be inserted into the eye through an incision of small size, typically about 2.5 millimeters (mm) to 4 mm. The ring of the capsular bag has an orifice at at least one of its ends suitable for receiving a hook fixed to the end of a wire which enables the entire ring to be inserted inside the cannula and subsequently ejected from the cannula once the end of the cannula is inserted in the eye. Putting the end of the ring into place on the hook of the injector requires a certain amount of handling which is quite difficult because of the small dimensions of the ring and of the hook at the end of the injector wire.

There therefore exists a real problem relating to putting the capsular bag ring into place inside the injector in order to enable it to be inserted into the eye.

Another object of the invention is to provide a system comprising a capsular bag ring associated with an injector to avoid the above-mentioned prior handling.

The capsular bag ring system is characterized in that it comprises:

a capsular bag ring comprising two asymmetrical branches presenting different radii of curvature; and a ring injector for putting said ring into place in the capsular bag, said injector comprising:
a cannula provided with an axial passage;
a body provided with a ring-handling mechanism, said mechanism comprising a flexible wire engaged in said axial passage, said wire having a first end provided with a handling member suitable for co-operating with the handling means of the ring to secure said wire temporarily to said ring, and a second end secured to means for moving said wire in said passage; and
in that when said handling member is secured to said handling means, said ring is engaged in the axial passage of said cannula via its second end over a suitable length of its second branch without applying any stress to the branch.

It will be understood that because, in accordance with the invention, the branch of the ring that is inserted in part into the cannula presents a radius of curvature that is much greater than that which is to be found in prior art rings, it is possible to insert one end of said branch into the cannula of the injector and to store the assembly until it is used by a surgeon.

Because of this large radius of curvature, the end of the second branch of the ring can remain stored in the cannula without that imparting significant deformation to the branch of the ring. It should be emphasized that such a disposition is not possible with standard type rings since the ends thereof present significant curvature which would give rise to stresses in the corresponding end of the ring likely to reduce its strength significantly after being stored for a certain length of time.

Other characteristics and advantages of the invention will appear better on reading the following description of various embodiments of the invention given as non-limiting examples. The description refers to the accompanying figures, in which:

BRIEF DESCRIPTION OF THE DRAWINGS

FIG. 2 is a longitudinal section view of a first embodiment of a ring injector;

FIGS. 3A and 3B are views in perspective and partially in section showing a portion of the FIG. 2 injector that enables it to be locked;

FIG. 4 is a fragmentary longitudinal section view showing the ring being put into place in the cannula of the injector;

DETAILED DESCRIPTION OF THE INVENTION

Figure 1:
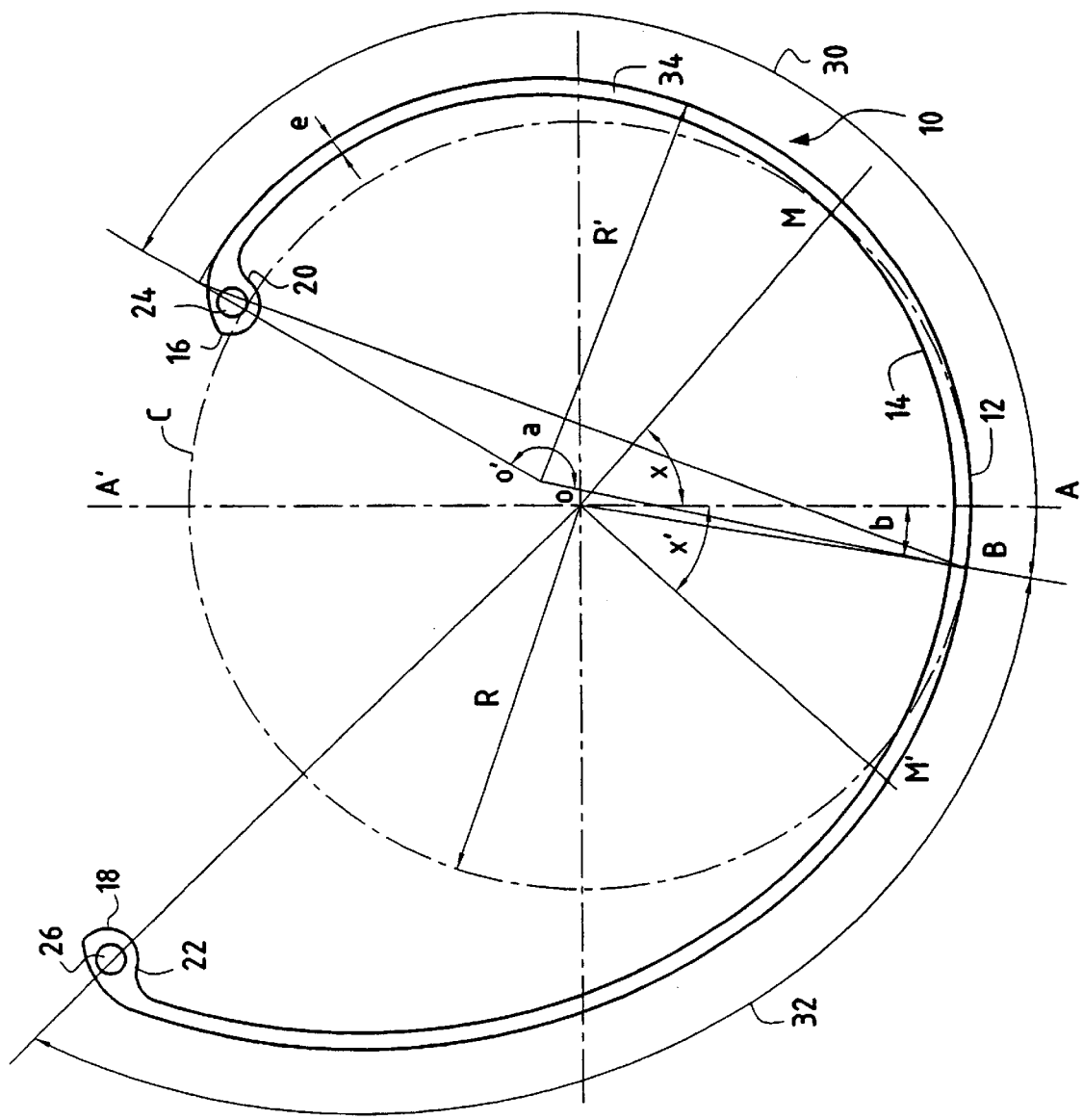
FIG. 1 is a plan view of a capsular bag ring of the invention.

With reference initially to FIG. 1, a capsular ring of the invention is described in its rest shape, i.e. the shape it takes up when no stress is applied thereto. It is preferably made of PMMA which is a material that is biocompatible and in widespread use for making intraocular implants, and in particular for making the haptic portions of such implants.

The ring 10 can be defined relative to a circle C of center O and radius R, said radius being substantially equal to the radius of the capsular bag in which the ring is to be installed. The ring 10 is tangential to the outside of the circle C at a point A. More precisely, the circle C is tangential to the outer edge 12 of the ring 10, said ring also having an inner edge 14. The ring is in the form of an elongate piece having a first end 16 and a second end 18. In this embodiment, the width of the ring, i.e. the distance between the edges 12 and 14 is constant. By way of example it can be equal to 0.17 mm. The thickness of the ring in a direction perpendicular to its plane of symmetry is substantially constant. For example it can be equal to 0.17 mm. Only the terminal portions 20 and 22 corresponding to the ends 16 and 18 are of increased width so as to make it possible to form holes 24 and 26 for handling the ring. The term "main" portion of the ring is used to designate its entire length with the exception of its terminal portions 20 and 22.

Returning to defining the shape of the ring, it has a first branch 30 extending from its first end 16 to a point B of the outer edge, said point B being offset from the tangential point A by an angle at the center of the circle C which is equal to b. The angle at the center b preferably lies in the range 1° to 15°, and the point B is situated on the same side of the median diameter AA' as is the second branch. The ring has a second branch 32 which extends from the point B to the second end of the ring 18.

The first branch 30 is general in the shape of a portion of a circle 34 of center O' and radius R', the center O' generally not coinciding with the center O of the circle C. The radius R' lies in the range R to R+10% of R. Relative to the center O' of the circular arc 34, the angle at the center a subtended by said circular arc at the point O' is less than 180°, and preferably greater than 120°.

It will be understood that the first branch 30 of the ring is generally in the form of a circular arc that is slightly smaller than a semicircle and that has a radius R' that is slightly greater than the radius of the capsular bag.

The outer edge 12 of the second branch 32 of the ring is defined by a hyperbolic spiral, or more precisely, by a portion of a hyperbolic spiral of center O. In the particular embodiment shown, the equation for the portion of a spiral in polar coordinates is $r=17/q$ where $q$ is the angle at the center.

Because of the shape of the branches 30 and 32 of the ring, it will be understood that when considering a point M' on the outer edge of the second branch 32 making an angle $x$ with the median diameter AA' of the circle C and also considering the point M on the outer edge of the first branch 30 that makes the same angle $x$ with the diameter AA', then the distance OM' is always greater than the distance OM. It will also be understood that the radius of curvature of the second branch 32 is much greater than the radius of curvature of the first branch, with said radius of curvature increasing on going away from the point B towards the second end 18 of the ring.

For the reasons described above relating to the shapes of the two branches of the ring, it will be understood that the ring can easily be put into place in the capsular bag.

FIG. 2 shows a ring injector 40. The injector comprises a cylindrical body 42 terminating in a conical portion 44 having a cannula fixed thereto, which cannula is in the shape of a circular arc 46. A piston 48 can move inside the body 42, the piston having a manual actuation head 50 and a second end 52 which is secured to the end of a wire 54 which can move inside the cannula 46 when the piston 48 moves. As explained in greater detail below, the wire 54 is terminated by a hook 56 enabling the second end 18 of the ring to be secured thereto because of the presence of the handling hole 26. A return spring 58 interposed between a shoulder 60 of the piston 48 and a shoulder 62 of the body of the injector tends to draw the wire 54 into the cannula 46. For reasons explained below, the injector 40 is preferably fitted with a removable clip-forming piece 64 including a stud 66 which can be engaged in holes 68 in the body of the injector and in a bore 70 in the piston 48 of the injector. When the piece 64 is in place, the piston 48 and thus the hook on the wire 54 of the injector are held stationary in a precise position which is set back by a length l from the opening 46a of the cannula.

Figure 5:
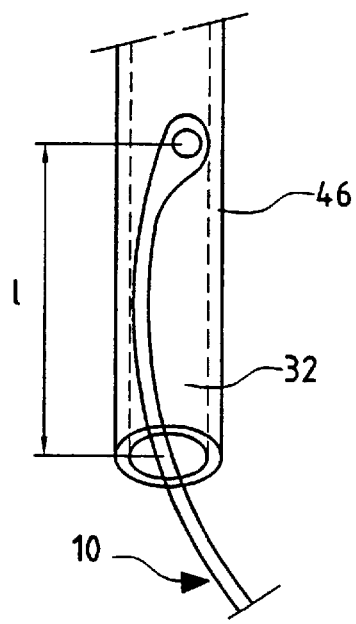
FIG. 5 is a view showing a detail of FIG. 4, showing the position of the end of the ring inside the cannula.

FIG. 4 shows the injector 40 fitted with a capsular bag ring 10 whose second end 18 penetrates through the end of the cannula and is secured to the wire 54 by means of the hook 56. As can be seen more clearly in FIG. 5, the second end of the second branch 32 of the ring 10 penetrates into the cannula 46 over a length l which is such that the end of the ring can be housed without any significant stress being applied thereto. As already explained, this particularly favorable result is obtained because the radius of curvature of the second end of the second branch 32 of the ring is much greater than that which is to be found in capsular bag rings of the state of the art.

The length l preferably lies in the range 4 mm to 5 mm.

Figure 6:
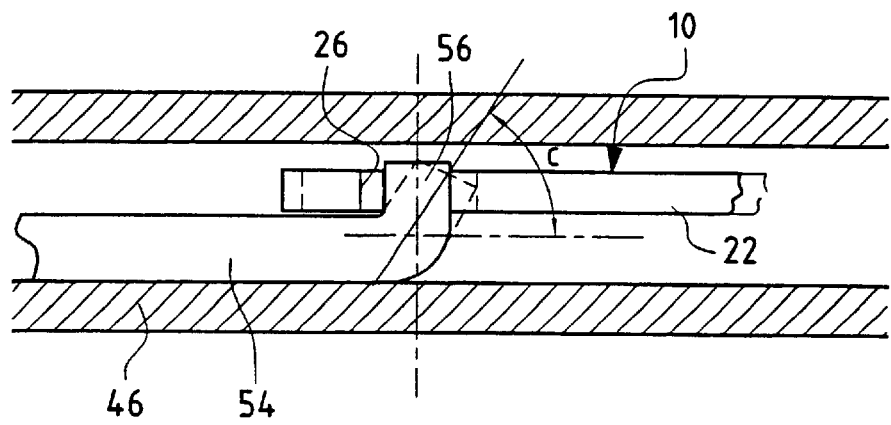
FIG. 6 shows an embodiment of the member for securing the ring to the cannula.

FIG. 6 shows a preferred embodiment of the hook 56 on the wire 54 of the injector in greater detail. It is constituted by an angled end portion of the wire. The angle c made by the angled portion relative to the main portion of the wire lies in the range 45° to 90°. It will be understood that because of the shape of the hook, it is held inside the hole 26 of the ring so long as the end of the ring remains inside the cannula 46. When this end is extracted therefrom, merely by moving the injector, the surgeon can separate the ring from the injector.

In a preferred embodiment, the cannula has an internal bore of elliptical section having axes of lengths 1.1 mm and 0.6 mm. The wire 54 has a diameter of 0.3 mm and the hole 26 has a diameter of 0.4 mm.

It will be understood that because no stress is applied to the end of the ring, the assembly constituted by the injector together with the ring 10 having its second end engaged inside the cannula of the injector and connected to the wire 54 of said injector can be stored for a long period of time. The assembly is placed in a pack that presents relative sealing that allows gas (ethylene oxide) to pass through for the purpose of sterilizing the assembly constituted by the injector and the ring.

Thus, when the surgeon seeks to put the ring into place in the capsular bag of a patient, the ring is already connected to the wire 54 of the injector. All the surgeon needs to do is to remove the clip-forming piece 64 and then the piston 48 moves rearwards under drive from the return spring causing the entire ring 10 to be drawn into the cannula 46. The surgeon then inserts the end 46a of the cannula into the patient's eye through the incision that has already been made, whereupon it suffices to press the piston so as to cause the ring to be expelled progressively, with the ring penetrating little by little into the capsular bag, beginning with its first branch which, as already explained, is substantially in the form of a semicircle corresponding substantially to the natural shape of the periphery of the capsular bag.

Figure 7:
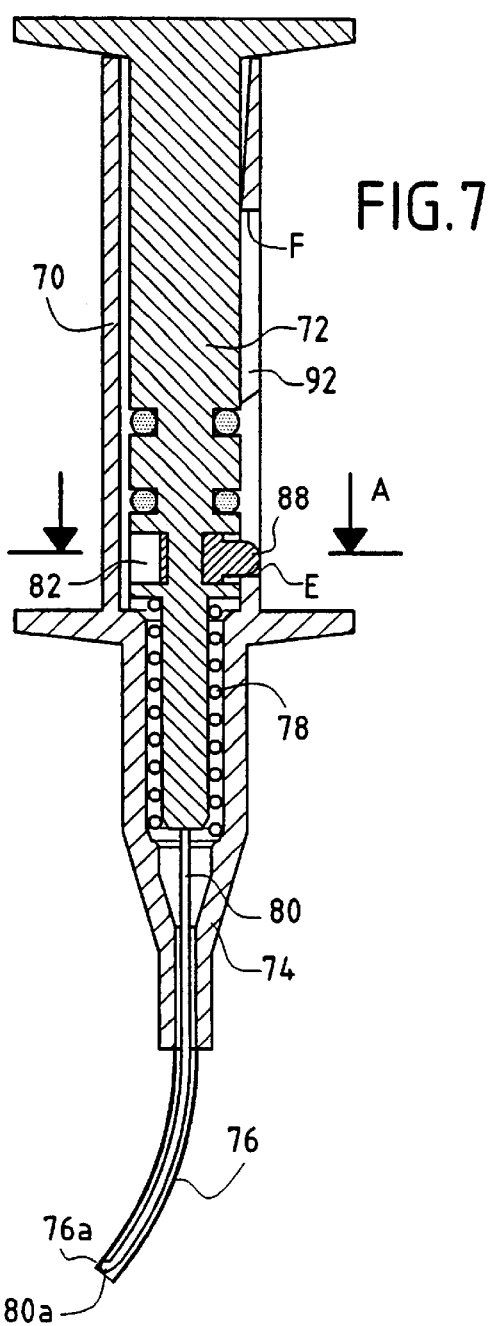
FIG. 7 is a longitudinal section view of a second embodiment of the injector.
Figure 7B:
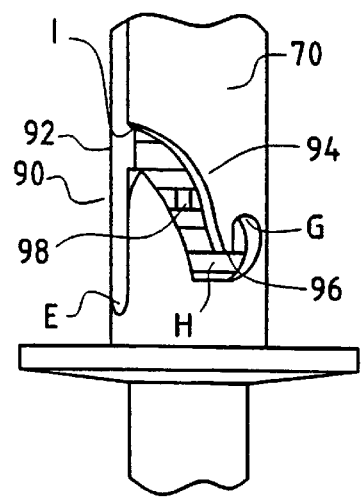
FIG. 7B is a fragmentary perspective view of the FIG. 7 injector.
Figure 7A:
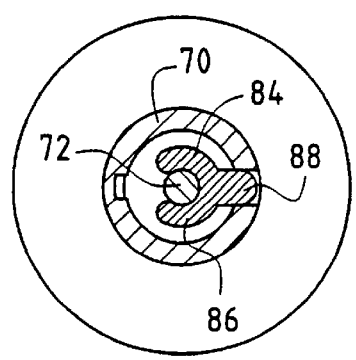
FIG. 7A is a section view on line A—A of FIG. 7.

FIGS. 7, 7A, and 7B show a second embodiment of the injector. This embodiment comprises a cylindrical hollow body 70 in which a piston 72 can move. The conical end 74 of the body 70 is fitted with a cannula 76 identical to the cannula 46 of FIG. 2. A return spring 78 urges the piston 72 away from the frustoconical end 74. A hook wire 80 is secured to the end 72a and can move inside the cannula 76.

The piston 72 has an annular groove 82 receiving a displacement member 84 constituted by a split ring 86 engaged in the groove 82 and by a displacement finger 88. The finger 88 is thus constrained to move in translation with the piston 72 but is free to rotate. The finger 88 penetrates into a slot 90 formed in the body 72 of the injector. The shape of the slot 90 can be seen more clearly in FIG. 7B. This slot has a rectilinear portion 92 parallel to the axis of the injector body and a deflected portion 94. The rectilinear portion 92 extends between a point E close to the frustoconical end and a point F (FIG. 7). When the finger 88 is in the position E, the wire 80 is fully extended from the cannula and the ring can be detached from the wire. When the finger 88 is in the position F, all of the ring is inside the cannula 76. This is the initial position for insertion.

The deflected portion 94 of the slot defines the storage position. The portion 94 of the slot comprises a first branch 96 extending between points G and H, the point G corresponding to the storage position of the ring in which only a very small portion of the ring is received inside the cannula as described above. The second branch 98 extends from the point H to a point I which connects with the rectilinear slot 92.

In the storage position, the finger 88 is held in stable manner in the position G under thrust from the spring 78 because of the bend constituted by the point H.

When the surgeon seeks to use the injector, it is necessary to apply pressure to the head of the piston 72 until the finger 88 has gone past the bend H in the diverted slot 94. From this position, under drive from the spring 78, the finger 88 follows the slot portion 96 and then the rectilinear slot 92 until it reaches the point F. The ring is then fully engaged inside the cannula. The assembly is ready for injecting the ring.

The surgeon then need only apply pressure to the head of the piston 72 in order to cause the ring to be ejected progressively from the cannula of the injector, with the finger 88 traveling along the rectilinear slot 92.

When the finger 88 reaches the point E, the ring is fully in place in the patient's eye and can be unhooked from the end of the wire 80.

What is claimed is:

1. A capsular bag ring to be implanted within the capsular bag of an eye, the capsular bag denoting a circle having a center O, a radius R and a tangential point A, said ring comprising an elongate element forming two asymmetrical branches having different radii of curvature, each branch of said element beginning at a connection point B and terminating in first and second ends respectively, each of said end having handling means, a first branch extending between said first end and said connection point B, and a second branch extending between said point B and said second end, said branches of said element lying in a plane and having a thickness that is constant in a direction that is orthogonal to said plane and said element having inner and outer edges, said elongate element having a length greater than the perimeter of said circle of said capsular bag and said outer edge of said first branch defining a portion of a circle of the center O' and radius R', where R<R'<1.10R, the outer edge of said elongate element defining a portion of a hyperbolic spiral of said center O and joining tangentially with said portion of said circle of center O' at said connection point B, whereby, a length of any segment joining the center O to a point M' of the outer edge of the second branch is greater than the length of a corresponding segment joining the center O of the circle to a point M' of the outer edge of the first branch, the point M being such that the angle between the segment OM and a median diameter joining the center O to a tangential point A is equal to the angle between the segment OM' and said median diameter; and wherein the radius of curvature at a point M' of the outer edge of the second branch is greater than the R'.

2. A ring according to claim 1, wherein at least said second end of said elongate element presents a terminal portion in said plane of symmetry that is of increased width, and wherein said handling means comprise a handling hole provided in said portion.

3. A ring according to claim 1, wherein said connection point B between said two branches is located on the same side of the median diameter as is said second branch.

4. A ring according to claim 1, wherein said elongate element is of substantially constant width between said inner and outer edges in its main portion.

5. A ring according to claim 1, including an angle (a), the apex of which is O', and corresponding to said first branch, is less than 180° and greater than 120°.

6. A ring according to claim 1, wherein said ring is made of PMMA.

7. A capsular bag ring system, comprising:

a capsular bag ring comprising an elongate element forming two asymmetrical branches having different radii of curvature, each branch of said element beginning at a connection point B and terminating in first and second ends respectively, each of said end having first securing means; and a ring injector for implanting said ring into a capsular bag of the eye, said injector comprising:
a cannula having an axial passage;
a body having a ring handling mechanism, said mechanism comprising a flexible wire engaged in said axial passage, said wire having a first end provided with second securing means suitable for engaging with said first securing means of the ring to secure said wire to said ring for implantation of the ring into the eye and insertion of the ring into said cannula, and a second end; and
moving means connected to said second end of said wire for moving said wire in said cannula,
whereby when said first securing means are secured to said second securing means, said ring can be maintained partially engaged in said axial passage of said cannula.

8. A ring system according to claim 7, further comprising a package containing said injector and said ring engaged in said cannula.

9. A ring system according to claim 8, wherein said package is made of a material that enables sterilization to be performed by means of a gas.

10. A capsular bag ring system, comprising:

a capsular bag ring comprising an elongate element forming two asymmetrical branches having different radii of curvature, each branch of said element beginning at a connection point B and terminating in first and second ends respectively, each of said end having a hole; and a ring injector for implanting said ring into a capsular bag of the eye, said injector comprising:
a cannula having an axial passage;
a body having a ring handling mechanism, said mechanism comprising a flexible wire engaged in said axial passage, said wire having a first end provided with a hook suitable for engaging with said hole of the ring to secure said wire to said ring for implantation of the ring into the eye and insertion of the ring into said cannula, and a second end; and
moving means connected to said second end of said wire for moving said wire in said cannula,
whereby when said hole is secured to said hook, said ring can be maintained partially engaged in said axial passage of said cannula.

* * * * *